(12) United States Patent
Busch

(10) Patent No.: US 6,843,104 B2
(45) Date of Patent: Jan. 18, 2005

(54) SAMPLING SYSTEM FOR EXHAUST GAS SENSORS AND METHOD OF USING SAME

(75) Inventor: Michael-Rainer Busch, Ebersbach (DE)

(73) Assignee: DaimlerChrysler AG, Stuttgart (DE)

( * ) Notice: Subject to any disclaimer, the term of this patent is extended or adjusted under 35 U.S.C. 154(b) by 0 days.

(21) Appl. No.: 10/353,091

(22) Filed: Jan. 29, 2003

(65) Prior Publication Data

US 2003/0172741 A1 Sep. 18, 2003

(30) Foreign Application Priority Data

Jan. 29, 2002 (DE) .......................... 102 03 310

(51) Int. Cl.[7] .................................................. G01N 7/00
(52) U.S. Cl. ...................................... 73/31.05; 73/23.31
(58) Field of Search ........................... 73/23.31, 23.32, 73/31.05; 204/424, 425, 426, 427, 428, 429

(56) References Cited

U.S. PATENT DOCUMENTS

| | | | | |
|---|---|---|---|---|
| 4,240,890 A | * | 12/1980 | Watanabe et al. | ........... 204/410 |
| 4,359,989 A | * | 11/1982 | Masaki et al. | .............. 123/438 |
| 4,534,213 A | * | 8/1985 | Mirikidani | ................. 73/118.1 |
| 4,622,009 A | * | 11/1986 | Bredeweg | .................... 432/156 |
| 4,795,614 A | * | 1/1989 | Norem et al. | .................. 422/94 |
| 5,012,670 A | * | 5/1991 | Kato et al. | .................. 73/31.05 |
| 5,423,972 A | * | 6/1995 | Mann et al. | ................. 204/424 |
| 5,450,749 A | * | 9/1995 | Strom et al. | ............... 73/117.3 |
| 6,346,179 B1 | * | 2/2002 | Makino et al. | ............. 204/428 |

FOREIGN PATENT DOCUMENTS

DE            297 06 003          9/1997

* cited by examiner

*Primary Examiner*—Michael Cygan
(74) *Attorney, Agent, or Firm*—Crowell & Moring LLP

(57) ABSTRACT

A system is provided for measuring gaseous constituents of a flowing gas mixture, having a gas flow control device and at least one sensor which is in contact with the flowing gas mixture. At least one mixing device is placed in the flow of the gas mixture, which mixing device homogenizes the gas mixture to mixed gas before it is detected by the sensor. The system is adapted for use in exhaust gas systems of internal-combustion engines.

21 Claims, 5 Drawing Sheets

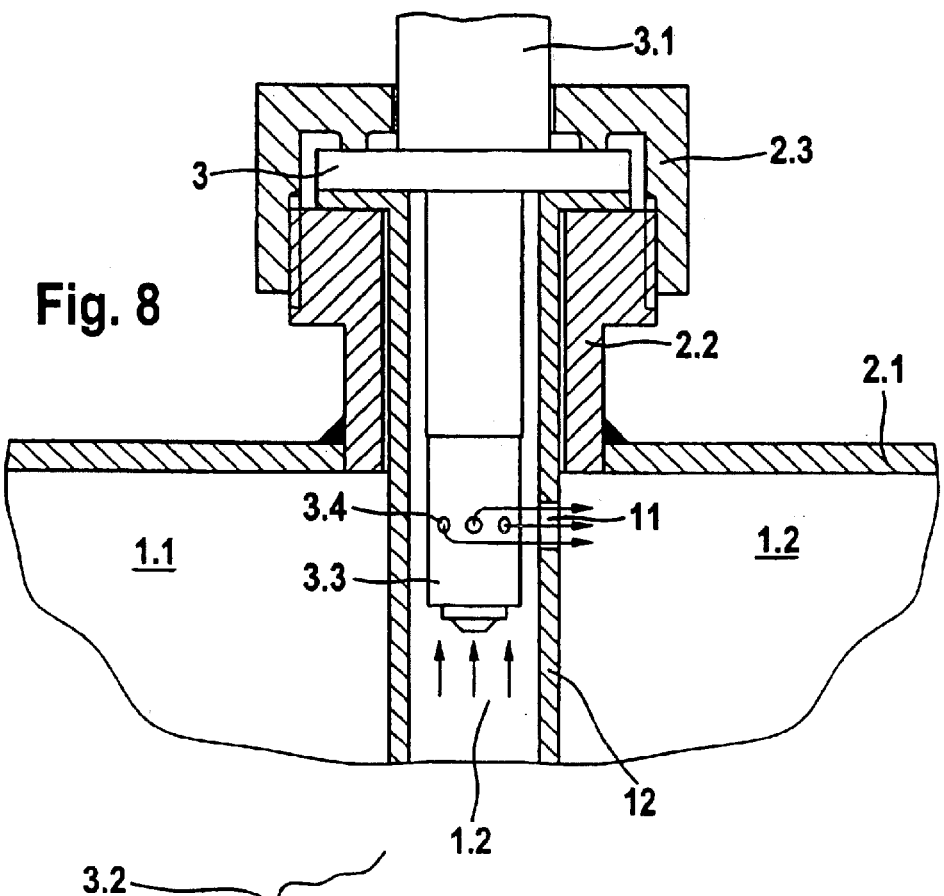
Fig. 8
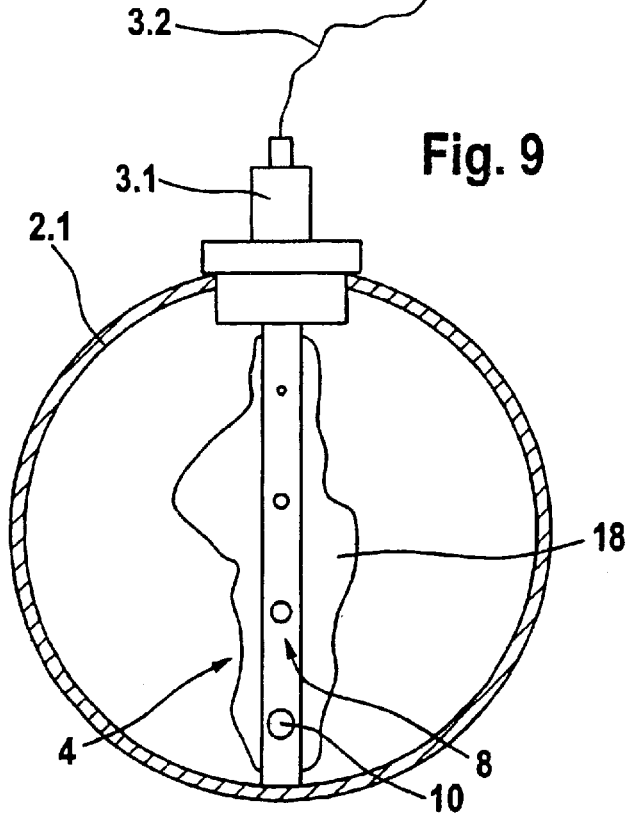
Fig. 9
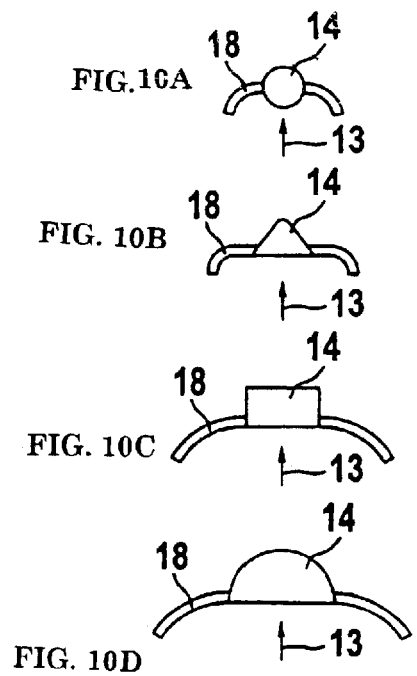
FIG. 10A
FIG. 10B
FIG. 10C
FIG. 10D

SAMPLING SYSTEM FOR EXHAUST GAS SENSORS AND METHOD OF USING SAME

BACKGROUND AND SUMMARY OF THE INVENTION

This application claims the priority of German Application No. 102 03 310.2 filed Jan. 29, 2002, the disclosure of which is expressly incorporated by reference herein.

The invention relates to a system for measuring gaseous constituents of a flowing gas mixture. The gas mixture moves in a gas flow control device and comes in contact with a sensor inserted there, which sensor detects individual gas constituents.

From German Patent Document DE 297 06 003 U1, an arrangement is known for measuring a flowing gas. This document describes a xenon gas sensor for monitoring and controlling the xenon concentration in flowing media. This xenon gas sensor has a thermal conductivity sensor and a hat-shaped covering of the sensor resistor. The oncoming flow should not take place in the direction of the opening of the hat-shaped covering of the thermal conductivity sensor.

It is an object of the invention to construct and arrange a system for the determination of the concentration of individual constituents of a flowing gas mixture such that the actual momentary concentration of the constituents to be measured is detected within the gas mixture.

According to the invention, the object is achieved in that at least one mixing device is inserted in the flow of the gas mixture, which mixing device homogenizes the gas mixture to mixed gas before it is detected by the sensor. As a result, it is achieved that filaments of flow existing in the gas mixture are swirled and mixed. In filaments of flow of turbulent or laminar flows, local absolute concentration fluctuations occur with respect to the actual momentary average value, which concentration fluctuations may well be in the one-digit percentage range ($10^{-2}$) or above. These local below-average or above-average momentary concentrations of different constituents of the gas mixture are compensated by the mixing device and homogenized mixed gas is fed to the sensor and faulty measurements are thereby avoided.

In exhaust gases of internal-combustion engines, such undesirable concentration fluctuations caused by filaments of flow occur more or less in the entire exhaust gas flow control device. Depending on the point at which, for example, a so-called lambda probe is situated as the sensor in the exhaust gas flow control device, filaments of flow are swirled by the system according to the invention. The momentary concentration of a constituent determined when the mixed gas is flowing therefore corresponds with a higher probability than without the mixing device to the absolute momentary concentration. The mixing device according to the invention should basically be applied at an arbitrary point in the exhaust gas flow control device, preferably in the front pipe, behind the high-performance header, in an exhaust muffler or in a section of the exhaust pipe. The lambda probe may be inserted particularly in front of or behind a catalyst or between two catalysts in the exhaust gas flow control device and the mixing device may be provided there.

For this purpose, it is advantageous that the mixing device homogenizes the entire portion or an approximately representative portion of the gas mixture flowing in the exhaust gas flow control device. In the most favorable case, a homogenizing of only 1% of the gas mixture may be sufficient; however, preferably approximately 20% are homogenized. For this purpose, the concentration of the individual constituents may be assumed, for example, to be approximately symmetrical along the cross-section of the gas flow control device. As a result, it may be sufficient to mix only a portion of the gas mixture which is to be considered as representative of the entire cross-section. After the mixing of a portion or of the entire gas mixture, the mixed gas will be accessible to the sensor. If only a portion of the gas mixture is mixed, the mixing device feeds the mixed gas to the sensor. Even when only a portion of the gas mixture is mixed, it may be advantageous to again feed only a portion or the entire mixed gas to the sensor. The quantity of the mixed gas fed to the sensor is, for example, also a function of the frequency at which the sensor measures and is preferably in the range of between 10% and 90%. If the entire gas mixture is detected by the mixing device, there is the possibility to mount the sensor at least behind the mixing device. In this case, it does not have to be provided directly behind the mixing device.

According to a further development of certain preferred embodiments of the invention, one possibility for mixing a portion of the gas mixture flow consists of providing the mixing device only in the center area in the direction of the diameter of the gas flow control device. Here, the mixing device projects from the pipe wall of the gas flow control device into the area of the center axis of the gas flow control device. In this case, the mixing device may have a distance from the opposite pipe wall or extend over the entire diameter. Another possibility consists of provided the mixing device along the entire inner circumference of the gas flow control device. Independently of the positioning and design of the mixing device, the latter forms a type of throttle in the gas flow control device. In this case, part of the pressure loss is utilized for the feeding of the mixed gas to the sensor.

Furthermore, it is advantageous according to certain preferred embodiments of the invention, that the cross-sectional surface of the mixing device varies perpendicularly to the flow direction. As a result, the range of the gas mixture removed for the measurement can be varied. The cross-sectional surface amounts to between 5% and 90%, preferably 15% of the flow cross-section of the gas flow control device. The cross-sectional surface is constructed to be either symmetrical or asymmetrical. Independently of its cross-sectional surface, the mixing device can be inserted directly or in an approximately radial direction through the housing wall of the gas flow control device. During the direct insertion, the mixing device is inserted with or without the sensor in the axial direction into the gas flow control device or is connected by means of an adapter piece into the flow.

It is also advantageous in this regard that the mixing device has at least one inlet opening and at least one outlet opening. The gas mixture entered through the inlet opening is deflected by means of a guiding device in its flow direction and is guided to the sensor. The outlet opening is provided directly at the sensor or in the proximity of the sensor. The gas mixture homogenized by the deflection is for the most part guided past the sensor and is analyzed or detected. The deflection of the flow direction causes the mixing of the gas mixture.

According to a preferred embodiment of the solution according to the invention, it is finally provided that the cross-sections of the inlet openings and outlet openings vary in their size and shape. It can be determined by a series of tests which opening cross-sections are advantageous for which flow parameters, such as the speed, the mass flow rate, the temperature and the composition.

The dimensioning of the mixing device, its shape and its arrangement also have an influence on the shape and position of the inlet and outlet openings. Not only the cross-sectional surface of the mixing device transversely to the flow direction, but also the cross-sections of the mixing device parallel to the flow direction may vary in their size and shape.

The mutual spacing of the inlet openings called the inlet spacing also has an influence on the finally determined measuring result. By varying the inlet spacing, the reliability of the sensor measurement can be improved, for example, when different temperature zones exist within the gas mixture.

It is particularly important according to certain preferred embodiments of the present invention that the size, the shape and the inlet spacing of the inlet and outlet openings with respect to one another varies as a function of the respective distance from the sensor. Preferably, the inlet and outlet openings become smaller with a decreasing distance from the sensor.

As an alternative to the forming of large inlet or outlet openings, these are formed by pores of the mixing device. For this purpose, sintered metals can be used which consist of metal or of a combination of ceramics and metal. Mixing devices are also provided which are formed exclusively of ceramics.

In connection with the construction and arrangement according to certain preferred embodiments of the invention, it is advantageous that the mixing device receives the sensor and is inserted into the gas flow control device together with the sensor. In this case, the sensor can be exchanged alone or together with the mixing device. The exchange takes place by way of an opening in the pipe wall of the gas flow control device or, depending on the insertion, by means of an intermediate piece of a pipe or similar device which is inserted as an adapter into the flow system.

It is also advantageous according to certain preferred embodiments of the invention that the mixing device, in addition to the guiding device, has at least one baffle plate situated on the outside. The baffle plate enlarges the detected flow cross-section and guides more gas mixture to the inlet openings. When used in an exhaust gas flow, the baffle plate heats up significantly faster than the mixing device and thus avoids the forming of condensate in the mixing device. Furthermore, as a result, the mixing device itself is heated more rapidly.

In this context, it is also advantageous according to certain preferred embodiments of the invention that the mixing device can additionally be heated by a heating device. The heating is independent of the use of a baffle plate. For the purpose of the heating, the mixing device accommodates an electrical heating device. In this case, the sensor is positioned such that it is not influenced by possible condensate and by the heating. By means of the heating device, the condensate occurring in or on the mixing device and on the sensor heats up and evaporates. The heating device can advantageously be started up already with the engine start or at least before the dew point of the exhaust gas flow has been reached. The formation of condensate is therefore prevented from the time of the start of the operation. According to certain preferred embodiments of the invention, the heating device is constructed as a grid-type heater, a wall heater or a rod-type heater inside the mixing device.

Additional advantages and details of the invention are explained in the claims and in the specification and are illustrated in the figures.

Other objects, advantages and novel features of the present invention will become apparent from the following detailed description of the invention when considered in conjunction with the accompanying drawings.

BRIEF DESCRIPTION OF THE DRAWINGS

FIG. 8 is a schematic sectional view of a device for inserting the sensor with the mixing device, constructed in accordance with a preferred embodiment of the invention;

FIG. 9 is a schematic sectional view perpendicular to the flow direction in front of the mixing device with an asymmetrical baffle plate, constructed in accordance with a preferred embodiment of the invention;

FIGS. 10A–10D are schematic sectional views parallel to the flow direction shown different mixing devices with the baffle plate, according to respective different preferred embodiments of the present invention;

DETAILED DESCRIPTION OF THE DRAWINGS

Figure 1:
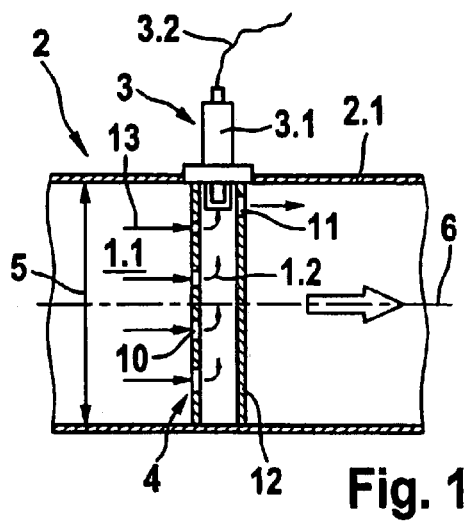
FIG. 1 is a schematic cross-sectional view of a pipe-shaped gas flow control device with a mixing device, constructed in accordance with a preferred embodiment of the invention.

FIG. 1 is a cross-sectional view of a pipe-shaped gas flow control device 2 with the mixing device 4. The mixing device 4 is inserted in the upper pipe wall 2.1. The sensor 3 is provided at the upper end of the mixing device 4. The sensor 3 has a sensor housing 3.1 and an electric sensor connection 3.2.

The lower end of the mixing device 4 rests against the opposite lower pipe wall 2.1. The mixing device 4 extends along the entire diameter 5 of the gas flow control device 2. The gas mixture 1.1 flows through the inlet openings 10 in the flow direction 13 parallel to the center axis 6 into the guiding device 12 of the mixing device 4. There, the gas mixture 1.1 is deflected perpendicularly to the flow direction 13 upward. This mixes the gas mixture 1.1. The resulting mixed gas 1.2 flows past the sensor 3 through the outlet opening 11 into the gas flow control device 2. In the process, the sensor 3 detects the individual gas constituents.

Figure 2:
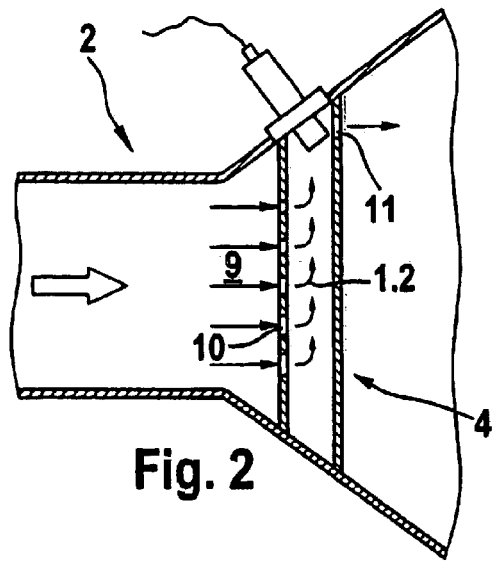
FIG. 2 is a schematic cross-sectional view of a funnel-shaped gas flow control device with the mixing device, constructed in accordance with a preferred embodiment of the invention.

FIG. 2 is a cross-sectional view of a funnel-shaped gas flow control device with the mixing device corresponding to FIG. 1. The inlet openings 10 are provided as a lengthening of the flow cross-section 9 on the mixing device. The mixing device 4 has only one outlet opening 11 through which the mixed gas 1.2 flows out again after the measuring by the sensor 3.

Figure 3:
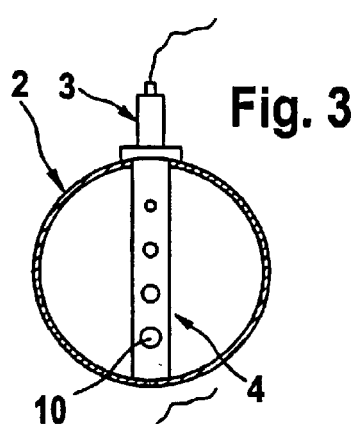
FIG. 3 is a schematic sectional view perpendicular to the flow direction in front of the mixing device with inlet openings, constructed in accordance with a preferred embodiment of the invention.
Figure 15:
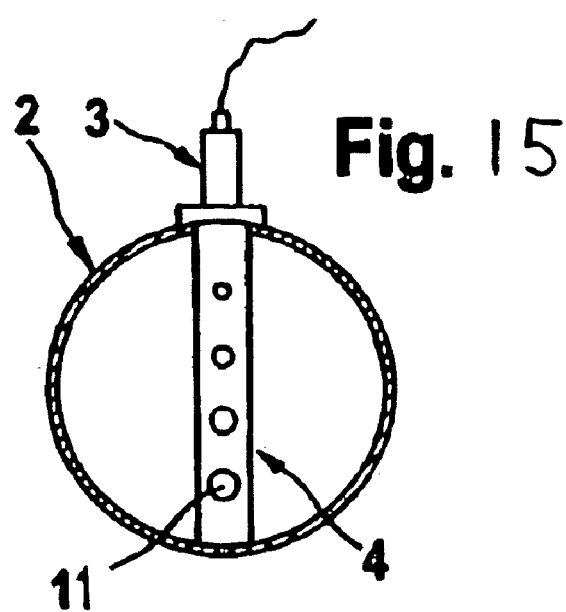
FIG. 15 is a schematic sectional view similar to FIG. 3 but showing outlet rather than inlet openings in accordance with a preferred embodiment of the invention.

FIG. 3 is a sectional view of the gas flow control device 2 perpendicular to the flow direction 13 with a view onto the mixing device 4. The mixing device 4 extends along the diameter 5 of the gas flow control device 2 and has several inlet openings 10. FIG. 15 is similar to FIG. 3 but shows an outlet rather than an inlet opening size which varies as a function of a distance of a respective outlet opening 11 from the sensor.

Figure 4:
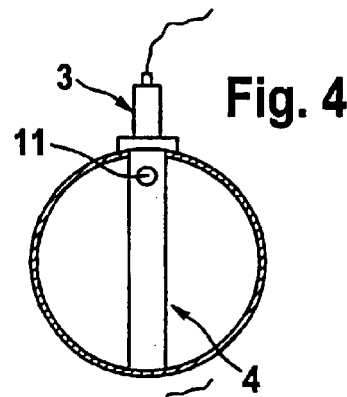
FIG. 4 is a schematic sectional view perpendicular to the flow direction behind the mixing device with the outlet opening, constructed in accordance with a preferred embodiment of the invention.

FIG. 4 shows an outlet opening 11 which is provided in the flow direction 13 on the side of the mixing device 4 opposite the inlet openings 10. The outlet opening 11 is provided in the area of influence of the sensor 3. Because of the mixing device 4, the sensor 3 is not visible.

Figure 5:
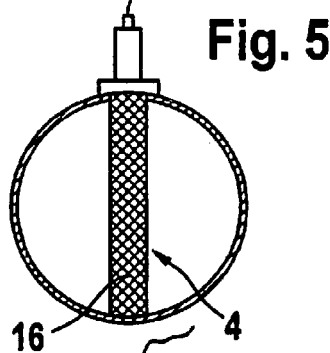
FIG. 5 is a schematic sectional view perpendicular to the flow direction in front of the mixing device with pores, constructed in accordance with a preferred embodiment of the invention.

As an alternative to the inlet openings 10 illustrated in FIG. 3, FIG. 5 shows a mixing device which is constructed of sintered metal. The entire mixing device 4 has pores 16 which are used as inlet openings 10 and as the outlet opening 11.

Figure 6:
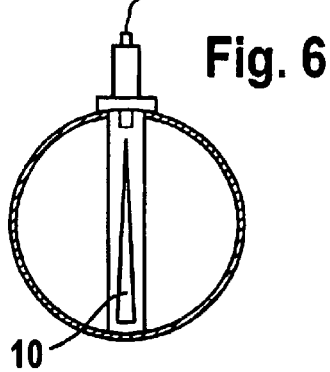
FIG. 6 is a schematic sectional view perpendicular to the flow direction in front of the mixing device with a slot-shaped inlet opening, constructed in accordance with a preferred embodiment of the invention.

As another alternative, FIG. 6 shows a slot-shaped inlet opening 10. Here, the outlet opening 11 is constructed corresponding to FIG. 4. The sensor 3 is situated in front of the outlet opening 11.

Figure 7:
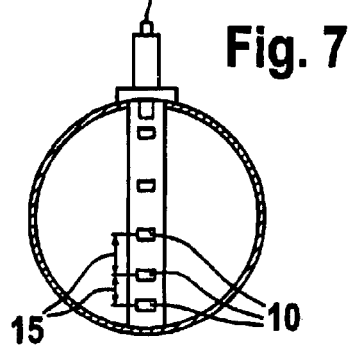
FIG. 7 is a schematic sectional view perpendicular to the flow direction in front of the mixing device with differently spaced inlet openings, constructed in accordance with a preferred embodiment of the invention.
Figure 16:
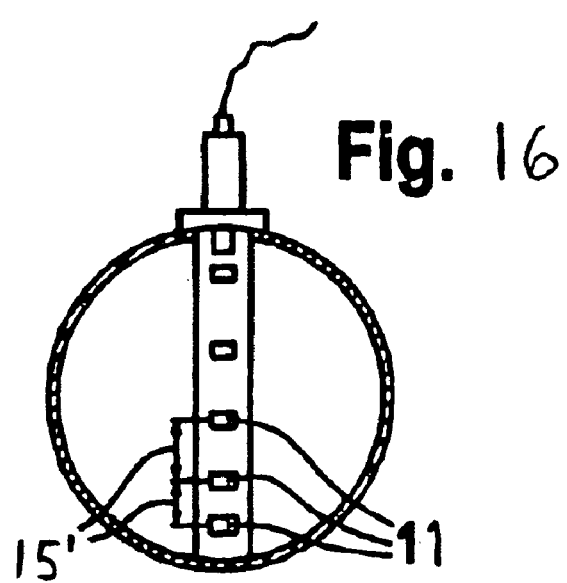
FIG. 16 is a schematic sectional view similar to FIG. 7 but showing differently spaced outlet rather than inlet openings.

FIG. 7 shows inlet openings 10 which have different inlet spacings 15. Also in this embodiment, the outlet opening 11 is constructed according to FIG. 4. FIG. 16 is similar to FIG. 7 but shows an outlet opening spacing 15' which varies as a function of a distance of a respective outlet opening 11 from the sensor.

FIG. 8 is a sectional view of a device for the insertion of the sensor 3 together with the mixing device 4. The device has a flange 2.2 welded to the pipe wall 2.1 of the gas flow control device 2. The guiding device 12 is inserted in the flange 2.2. The sensor 3 is inserted in the guiding device 12. The head of the sensor 3 projects into the area of the outlet opening 11. In order to fix the sensor 3 with the sensor housing 3.1, these components are fastened to the flange 2.2 by means of a union nut 2.3.

After the deflection in the guiding device 12, the gas mixture 1.1 is mixed to mixed gas 1.2 and flows into the sensor head 3.3. For a flow around the sensor 3, the sensor head 3.3 has holes 3.4. The holes 3.4 are provided in the area of the outlet opening 11.

FIG. 9 is a sectional view of the gas flow control device 2 perpendicular to the flow direction 13. The mixing device 4 has an asymmetrical baffle plate 18. The baffle plate 18 is used for detecting and guiding the gas mixture 1.1 to the inlet opening 10.

FIGS. 10A–10D show different possible cross-sectional views 14 of mixing devices 4 with a baffle plate 18. The baffle plates 18 guide the gas mixture 1.1 into the openings of the mixing device 4. The various mixing devices 4 differ essentially in the cross-sectional profile and in the span of the baffle plates 18.

Figure 11:
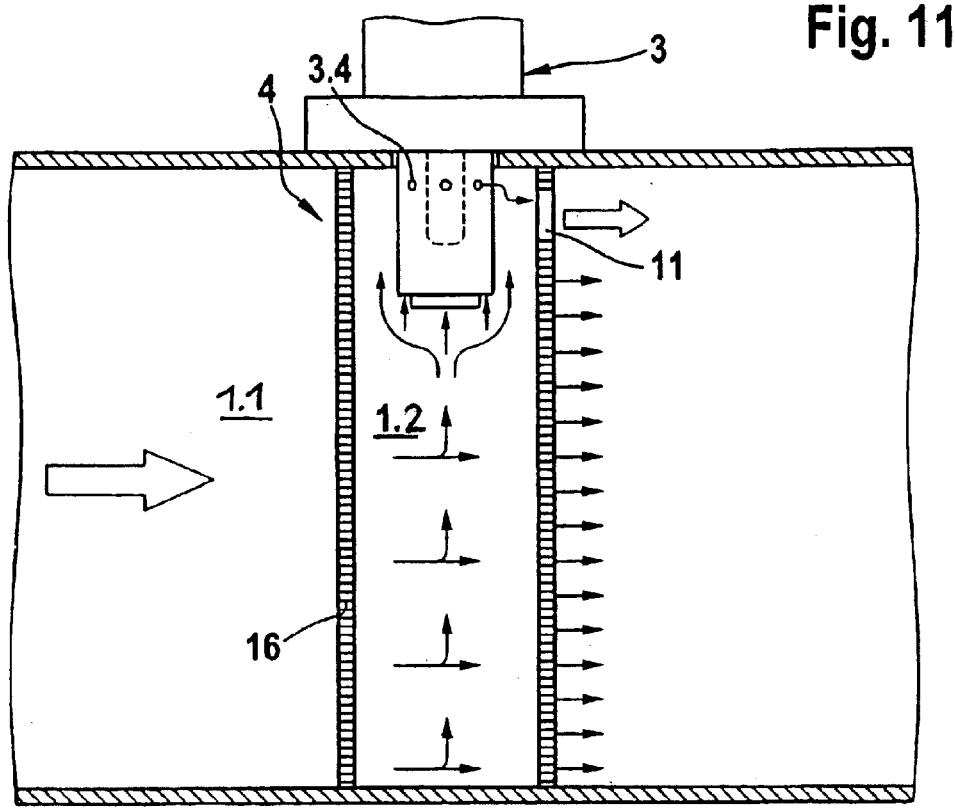
FIG. 11 is a schematic sectional view of a mixing device with pores, constructed in accordance with a preferred embodiment of the invention.

FIG. 11 is a sectional view of a mixing device 4 with a net-type structure and pores 16 consisting of a sintered metal. The holes 3.4 are provided above the outlet opening 11. Because of the pressure differences in front of, behind and in the guiding device 12, the gas mixture 1.1 is deflected in the upward direction. The positioning of the sensor 3 with respect to the outlet opening 11 influences the measurement and the measuring result.

Figure 12:
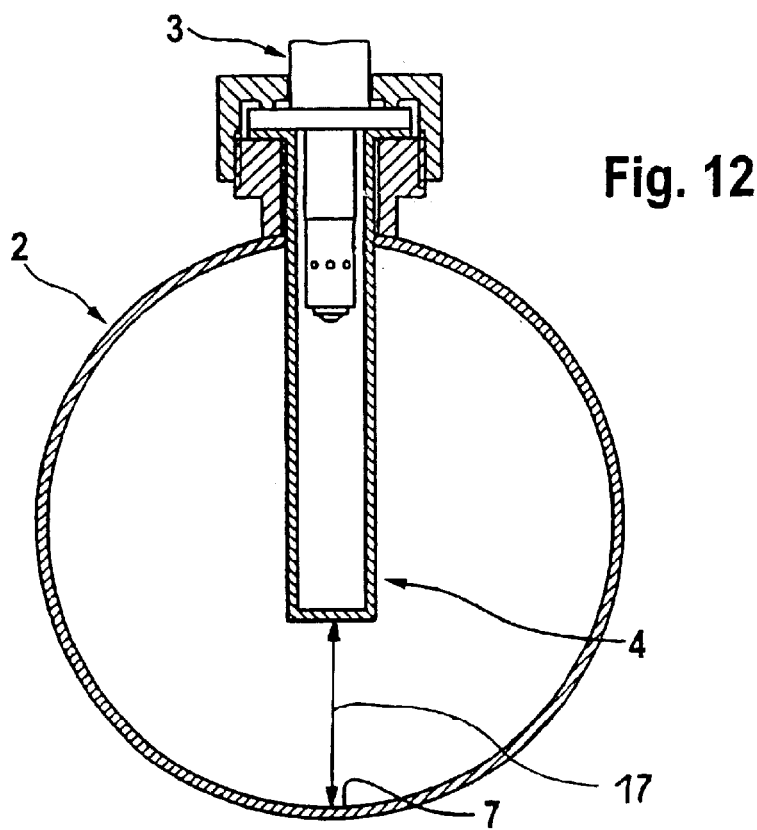
FIG. 12 is a schematic sectional view of a device for inserting the sensor with a spaced mixing device, constructed in accordance with a preferred embodiment of the invention.

FIG. 12 is a sectional view of a device for inserting the sensor 3. The mixing device 4 is spaced at a distance 17 with respect to the wall area 7 and is inserted into the gas flow control device 2 corresponding to FIG. 8.

Figure 13:
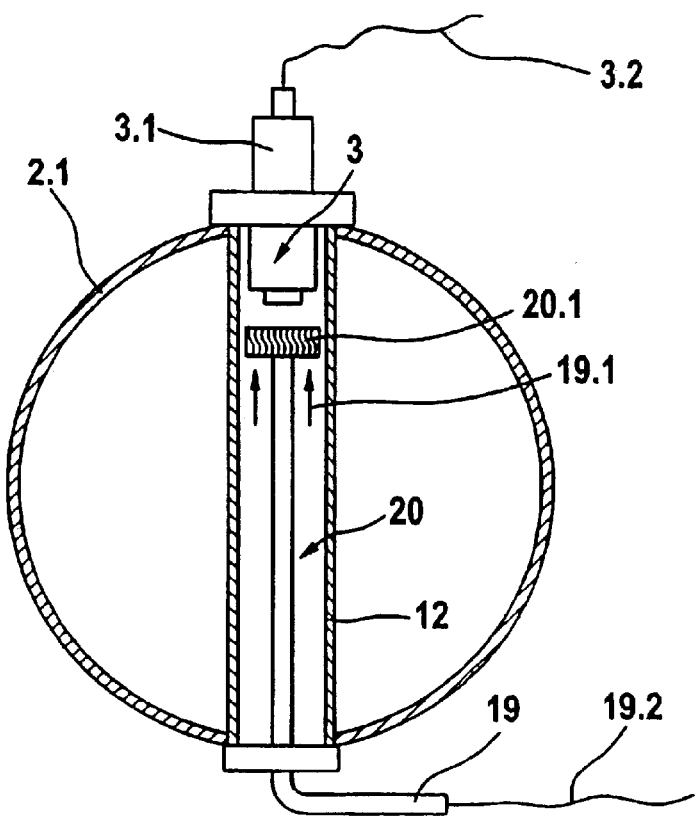
FIG. 13 is a schematic sectional view of a device for inserting a grid-shaped heating device with the mixing device, constructed in accordance with a preferred embodiment of the invention.
Figure 14:
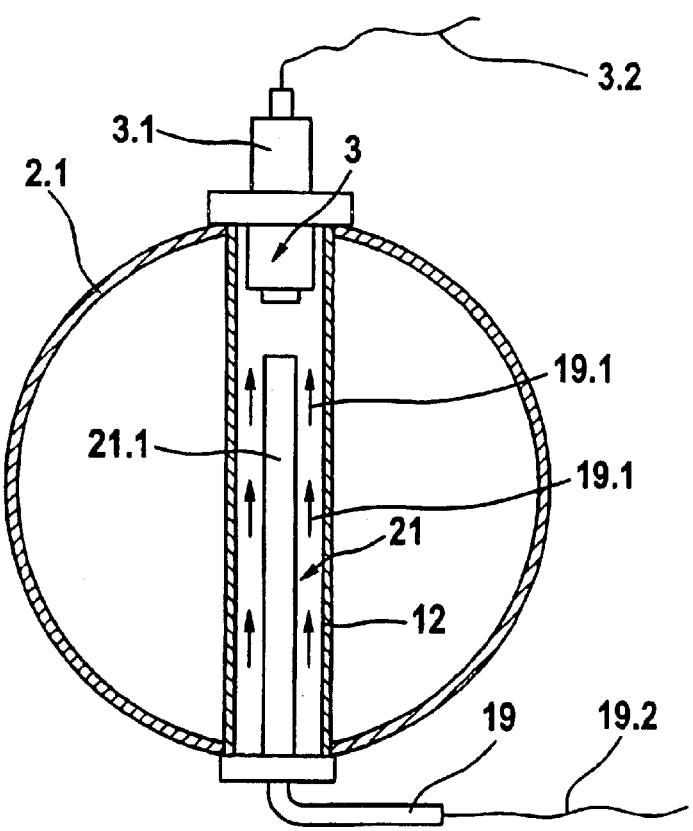
FIG. 14 is a schematic sectional view of a device for inserting a rod-shaped heating device with the mixing device, constructed in accordance with a preferred embodiment of the invention.

According to FIGS. 13 and 14, the mixing device 4 can be heated by means of a heating device 19. As a result, the condensate which occurs in the mixing device 4 and possibly at the sensor 3 is evaporated. In FIG. 13, the heating device 19 is constructed as a grid-type heater 20 having a heating grid 20.1. In FIG. 14, the heating device 19 is constructed as a rod-type heater 21 having a heating rod 21.1.

The heating device 19 is inserted into the mixing device 4 within the pipe wall 2.1. The sensor 3 with the sensor housing 3.1 and the sensor connection 3.2 is situated above the heating device 19. By way of power cable 19.2, the heating device 19 is supplied with energy in a controlled manner. In addition to the mixing device 4, the exhaust gas flow 19.1 is heated within the mixing device 4. The thermal current of the exhaust gas flow 19.1 is promoted by the heating. The proximity of the heater to the sensor 3 contributes to avoiding condensate on the heater 3.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. System for measuring gaseous constituents of a flowing gas mixture comprising:
    a gas flow control device;
    at least one sensor which is in use in contact with the flowing gas mixture; and
    at least one mixing device inserted in a flow of the gas mixture, the mixing device having a first end at which the at least one sensor is provided and a second end adapted to rest against a wall of a pipe through which the gas mixture can flow, and in use homogenizing the gas mixture to mixed gas before it is detected by the sensor.

2. System according to claim 1, wherein the mixing device is operable to homogenize between 1% and 100% of the gas mixture flowing in the gas flow control device; and wherein the mixing device feeds between 10% and 90% of the mixed gas to the sensor.

3. System according to claim 2, wherein the mixing device is operable to homogenize approximately 20% of the gas mixture flowing in the gas flow control device.

4. System according to claim 2, wherein the mixing device extends over the entire diameter of the gas flow control device.

5. System according to claim 1, wherein a cross-sectional surface of the mixing device perpendicular to a flow direction amounts to between 5% and 90% of a flow cross-section of the gas flow control device.

6. System according to claim 1, wherein the mixing device is inserted through the wall of the pipe.

7. System according to claim 5, wherein the cross-sectional surface of the mixing device perpendicular to the flow direction amounts to approximately 15% of the flow cross section of the gas flow control device.

8. System according to claim 1, wherein the mixing device has at least one inlet opening and at least one outlet opening; and
   wherein a guiding device is provided between the at least one inlet opening and the at least one outlet opening, which guiding device deflects the gas mixture received through the at least one inlet opening in its flow direction.

9. System according to claim 2, wherein the mixing device has at least one inlet opening and at least one outlet opening; and
   wherein a guiding device is provided between the at least one inlet opening and the at least one outlet opening, which guiding device deflects the gas mixture received through the at least one inlet opening in its flow direction.

10. System according to claim 5, wherein the mixing device has at least one inlet opening and at least one outlet opening; and
    wherein a guiding device is provided between the at least one inlet opening and the at least one outlet opening, which guiding device deflects the gas mixture received through the at least one inlet opening in its flow direction.

11. System according to claim 1, wherein the at least one mixing device has a plurality of inlet openings and at least one outlet opening, and wherein the cross-sections of the inlet openings vary in at least one of shape and size, the inlet openings vary in their inlet spacing with respect to one another, the inlet openings are formed by pores, or the at least one outlet opening is one of a plurality of outlet openings are formed by pores.

12. System according to claim 1, wherein a surface forming at least one of the inlet openings and the outlet openings of the mixing device is formed of one of metal and ceramics.

13. System according to claim 1, wherein the mixing device accommodates the sensor and/or is inserted together with the sensor into the gas flow control device and can be exchanged together with the sensor.

14. System according to claim 8, wherein in addition to the guiding device, the mixing device has at least one baffle plate which is situated on an outside of the mixing device and which guides the gas mixture into the at least one inlet opening.

15. System according to claim 1, wherein the mixing device can be heated by a heating device or receives a heating device.

16. System according to claim 1, wherein the flowing gas mixture is an exhaust flow mixture from a combustion engine.

17. A method of using the system of claim 1, comprising measuring an exhaust flow mixture from a combustion engine.

18. A system for measuring gas constituents of an exhaust gas flow mixture from a combustion engine of a motor vehicle comprising:
    a gas flow control device;
    at least one sensor which is in use in contact with the flowing gas mixture; and
    at least one mixing device inserted in a flow of the gas mixture, the mixing device having a first end at which the at least one sensor is provided and a second end adapted to rest against a wall of a pipe through which the gas mixture can flow, and in use homogenizing the gas mixture to mixed gas before it is detected by the sensor.

19. A system according to claim 18, wherein the mixing device is operable to homogenize between 1% and 100% of the gas mixture flowing in the gas flow control device; and wherein the mixing device feeds between 10% and 90% of the mixed gas to the sensor.

20. A system according to claim 19, wherein the mixing device is operable to homogenize approximately 20% of the gas mixture flowing in the gas flow control device.

21. A system according to claim 2, wherein a cross-sectional surface of the mixing device perpendicular to a flow direction amounts to between 5% and 90% of a flow cross-section of the gas flow control device.

* * * * *